United States Patent [19]

Herzog et al.

[11] 3,985,877

[45] Oct. 12, 1976

[54] AZIDO-S-TRIAZINE INSECTICIDES

[75] Inventors: Alexis Herzog; Hans Ulrich Brechbuehler, both of Basel, Switzerland

[73] Assignee: Ciba-Geigy Corporation, Ardsley, N.Y.

[22] Filed: Dec. 4, 1974

[21] Appl. No.: 529,428

Related U.S. Application Data

[63] Continuation-in-part of Ser. No. 252,729, May 12, 1972, Pat. No. 3,853,868.

[30] Foreign Application Priority Data

June 1, 1971 Switzerland.......................... 7925/71
Apr. 10, 1972 Switzerland.......................... 5214/72

[52] U.S. Cl. ............................................... 424/249
[51] Int. Cl.² ........................ A01N 9/00; A01N 9/22
[58] Field of Search............................ 424/226, 249; 260/249.6

[56] References Cited
UNITED STATES PATENTS

| 3,238,230 | 3/1966 | Haszeldine et al.................. 260/349 |
| 3,497,511 | 2/1970 | Schwarze et al............. 260/249.6 X |
| 3,583,987 | 6/1971 | Berrer et al...................... 260/249.6 |
| 3,634,423 | 1/1972 | Schwarze..................... 260/249.6 X |

OTHER PUBLICATIONS
Annual Rev. of Biochem., 40, 781, 1096–1097, (1971), K. Slama, "Insect Juvenile Hormone Analogues."

Primary Examiner—Leonard Schenkman
Assistant Examiner—D. W. Robinson
Attorney, Agent, or Firm—Harry Falber

[57] ABSTRACT

Method and composition for combating insects comprising the use of s-triazine derivatives of the formula

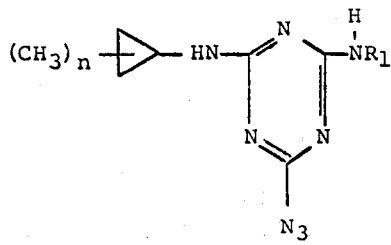

wherein $R_1$ represents hydrogen, cyclopropyl, 1-methylcyclopropyl, 2-methylcyclopropyl, $C_1$–$C_5$ alkyl, $C_3$–$C_4$ alkenyl, $C_3$–$C_4$ alkynyl, or $C_1$–$C_5$ alkyl substituted by cyano and $n$ represents 0 or 1.

6 Claims, No Drawings

AZIDO-S-TRIAZINE INSECTICIDES

RELATED APPLICATION

This application is a continuation-in-part of copending application Ser. No. 252,729, filed May 12, 1972, now U.S. Pat. No. 3,853,868.

The present invention relates to a method of combating insects which comprises the use of s-triazine derivatives of the formula

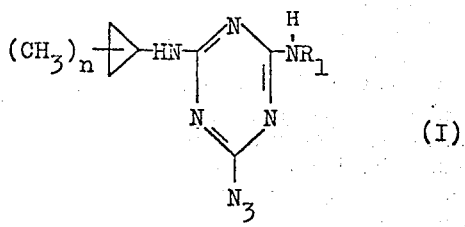

wherein $R_1$ represents hydrogen, cyclopropyl, 1-methylcyclopropyl, 2-methylcyclopropyl, $C_1$–$C_5$ alkyl, $C_3$–$C_4$ alkenyl, $C_3$–$C_4$ alkynyl or $C_1$–$C_5$ alkyl substituted by cyano, and $n$ represents 0 or 1.

The $C_1$–$C_5$ alkyl radicals which are possible for $R_1$ may be branched or straight-chain.

Examples of such radicals include: methyl, ethyl, propyl, isopropyl, n-, i-, sec- and tert.butyl.

Examples of cyanoalkyl radicals which are possible for $R_1$ include: 1-cyanoethyl, 1-cyanopropyl, 2-cyanobut-2-yl, 3-cyano-pent-3-yl.

Preferred $C_3$–$C_4$ alkenyl or $C_3$–$C_4$ alkynyl radicals for $R_1$ are the allyl and propargyl radicals.

Compounds of particular importance are those of the formula

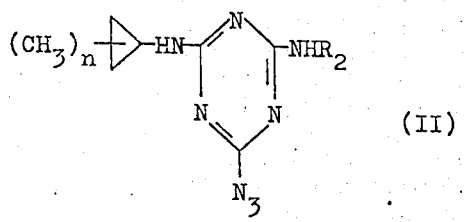

wherein $R_2$ represents cyclopropyl, 2-methylcyclopropyl, methyl, ethyl, n-propyl, isopropyl, n-, i-, sec.- and tert.butyl, 1-cyanoethyl, 1-cyanopropyl, and $n$ represents 0 or 1.

The following compounds may be cited as examples of suitable compounds of the formula II:

| Compound | | m.p.: °C |
|---|---|---|
| 1. | 4-azido-2-methylamino-6-cyclopropylamino-s-triazine | 93–98 |
| 2. | 4-azido-2-ethylamino-6-cyclopropylamino-s-triazine | 82–83 |
| 3. | 4-azido-2-isopropylamino-6-cyclopropylamino-s-triazine | 80–85 |
| 4. | 4-azido-2-sec. butylamino-6-cyclopropylamino-s-triazine | 73–78 |
| 5. | 4-azido-2-tert. butylamino-6-cyclopropylamino-s-triazine | 95–97 |
| 6. | 4-azido-2,6-bis-cyclopropylamino-s-triazine | 105–107 |
| 7. | 4-azido-2-isobutylamino-6-cyclopropylamino-s-triazine | 93–94 |
| 8. | 4-azido-2-(2'-cyanobut-2'-ylamino)-6-cyclopropylamino-s-triazine | 106–108 |
| 9. | 4-azido-2-(3'-cyanopent-3'-ylamino)-6-cyclopropylamino-s-triazine | 112–114 |
| 10. | 4-azido-2-(1'-cyanoethylamino)-6-cyclopropylamino-s-triazine | 121–123 |
| 11. | 4-azido-2-(1'-cyanoprop-1'-ylamino)-6-cyclopropylamino-s-triazine | 78–80 |
| 12. | 4-azido-2-ethylamino-6-(2'-methylcyclopropylamino)-s-triazine | 98–102 |
| 13. | 4-azido-2-amino-6-cyclopropylamino-s-triazine | 131–132.5 |
| 14. | 4-azido-2-allylamino-6-cyclopropylamino-s-triazine | 56.5–58.5 |
| 15. | 4-azido-2-propargylamino-6-cyclopropylamino-s-triazine | 115–116 |

The invention also relates to new compounds, process for their manufacture and to pesticidal agents which contain these compounds as active ingredients.

The new compounds have the formula

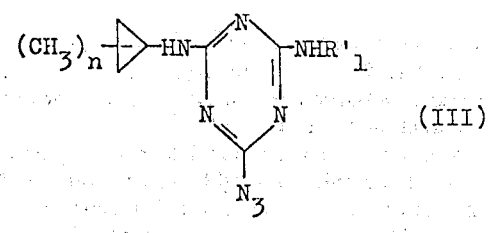

wherein $R_1'$ represents hydrogen, $C_3$–$C_4$ alkenyl or $C_3$–$C_4$ alkynyl and $n$ represents 0 or 1.

Preferred $C_3$–$C_4$ alkenyl or $C_3$–$C_4$ alkynyl radicals for $R_1'$ are the allyl and propargyl radicals.

The compounds of the formula I are manufactured by reacting a chloro-bis-amino-s-triazine of the formula

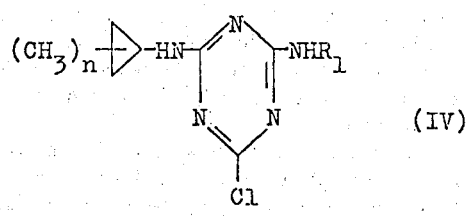

wherein $n$ and $R_1$ have the meanings given for the formula I, with an alkali metal azide in the presence of a base, or by reacting the compound of the formula IV with hydrazine and reacting the resulting hydrazino-s-triazine of the formula

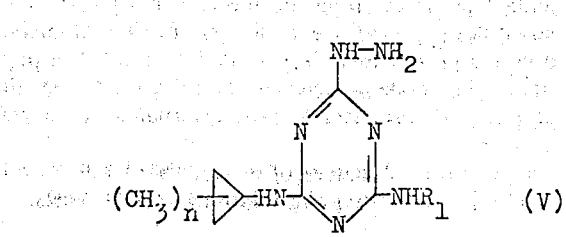

wherein *n* and $R_1$ have the meanings given for the formula I, with nitrous acid or an alkali metal nitrite, or by reacting the compound of the formula

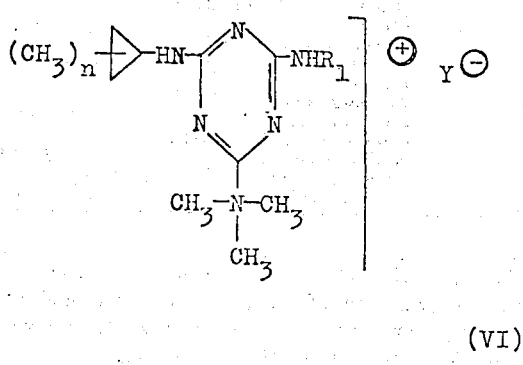

(VI)

wherein $R_1$ and n have the meaning given for the formula I and Y represents an inorganic or organic acid radical, in particular chlorine, bromine or iodine, with an alkali metal azide.

Suitable bases are in particular tertiary amines, such as trialkyl amines, also hydroxides, oxides and carbonates of alkali and alkaline earth metals. Water is used preferably as solvent or diluent for the reactions; but it is also possible to use organic solvents which are miscible with water, such as ketones, ethers and ether-like compounds, nitriles, N,N-disubstituted amides, sulphoxides etc., also solvents which are immiscible with water, for example aliphatic and aromatic hydrocarbons and halogenated hydrocarbons.

Analogous compounds are described in Belgian Pat. No. 730,133 as total herbicides and selective herbicides.

Analogous compounds are also described as herbicides in French Pat. No. 1,537,312, and attention is drawn to their possible insecticidal action.

In comparison to these active substances, the compounds of the formula I display a distinct superiority in the fly test.

It is a commonly known fact that phosphoric acid esters, as representatives of classical insecticides, kill both vertebrates and invertebrates by cholinesterase inhibition through the accumulation of acetyl choline at the nerve endings. The accumulated acetyl choline severely disrupts the function of the nervous system and death occurs as a consequence after a few hours. In contrast to the classical insecticides, which, in the form of contact or stomach poisons, kill or paralyse the insects in a few hours, the active compounds of the formula I primarily influence the terminal phase of the larval development. Depending on the time of application, the development is arrested in the larval or pupal stage. This mode of action is not comparable with that of classical insecticides, chemosterilants or juvenile hormones.

The active substances of the formula I can be used chiefly for combating the following hygiene pests:

| Diptera | Culicidae |
|---|---|
| | Simuliidae |
| | Tipulidae |
| | Muscidae |
| | Calliphoridae |

The compounds of the formula I can be used as pure concentrate or together with suitable carriers and/or additives. Suitable carriers and additives can be solid or liquid and correspond to the substances conventionally used in formulation technique such, for example, as solvents, dispersants, wetting agents, adhesives, thickeners, binders and/or fertilisers.

The agents according to the invention are manufactured in known manner by intimately mixing and/or grinding active compounds of the formula I with the suitable carriers, optionally with the addition of dispersants or solvents which are inert towards the active substances. The active substances may be applied in the following forms:

Solid forms dusts, granules, coated granules, impregnated granules and homogeneous granules, premix (feed additive).

Liquid forms a. active compound which are dispersible in water: wettable powders, pastes, émulsions;
b. solutions: aerosols.

To manufacture solid forms (dusts) the active compounds are mixed with solid carriers. Suitable carriers are, for example: kaolin, talcum, bolus, loess, chalk, limestone, ground limestone, attaclay, dolomite, diatomaceous earth, precipitated silica, alkaline earth silicates, sodium and potassium aluminium silicates (feldspar and mica), secondary calcium phosphate, calcium and magnesium sulphates, magnesium oxide, ground synthetic materials, fertilisers, for example ammonium sulphate, ammonium phosphate, ammonium nitrate, urea, ground vegetable products, such as corn meal, bark dust, sawdust, nutshell meal, cellulose powder, residues of plant extractions, activated charcoal etc. These substances can either be used along or in admixture with one another.

Granules can be manufactured by dissolving an active compound of the formula I in an organic solvent and applying the resulting solution to a granulated material, for example attapulgite, $SiO_2$, granicalcium, bentonite etc. and then evaporating the solvent.

Polymer granules can also be manufactured by mixing the active compound of the formula I with polymerisable compounds (urea/formaldehyde; dicyandiamide/formaldehyde; melamine/formaldehyde or others), whereupon a mild polymerisation is carried out that does not affect the active compound and in the process of which the granulation is carried out during the gel formation. It is more advantageous to impregnate finished, porous polymer granules (urea/formaldehyde, polyacrylonitrile, polyesters or others) which have a specific surface area and a favourable predeterminable adsorption/desorption ratio, with the active compounds, for example in the form of their solutions (in a low boiling solvent) and to remove the solvent. Polymer granules of this kind in the form of microgranules having a bulk density of 300 g/liter to 600 g/liter can also be manufactured with the aid of atomisers. The dusting can be carried out from aircraft.

Granules can also be obtained by compacting active ingredients, carriers and additives and subsequent pulverization.

To these mixtures can also be added additives which stabilize the active compound and/or non-ionic, anionic and cationic surface active substances, which for example improve the adhesion of the active ingredients on plants or parts of plants (adhesives and agglutinants) and/or ensure a better wettability (wetting agents) and dispersibility (dispersing agents). The following substances, for example, are suitable: olein/chalk mixture, cellulose derivatives (methyl cellulose, carboxymethyl cellulose), hydroxyethyl glycol ethers of monoalkyl and dialkyl phenols having 5 to 15 ethylene oxide radicals per molecule and 8 to 9 carbon atoms in the alkyl radical, lignin sulfonic acids, their alkali metal and alkaline earth metal salts, polyethylene glycol ethers (carbowaxes), fatty alcohol polyethylene glycol ethers having 5 to 20 ethylene oxide radicals per molecule and 8 to 18 carbon atoms in the fatty alcohol moiety, condensation products of ethylene oxide/propylene oxide, polyvinyl pyrrolidones, polyvinyl alcohols, condensation products of urea and formaldehyde, and also latex products.

The water-dispersible concentrates of the active ingredients, i.e. wettable powders, pastes and emulsifiable concentrates, are agents which can be diluted with water to any concentration desired. They consist of active ingredients carrier, optional additives which stabilize the active ingredients surface-active ingredients and anti-foam agents and, optionally, solvents.

Wettable powders and pastes are obtained by mixing and grinding the active ingredients with dispersing agents and pulverulent carriers in suitable apparatus until homogeneity is attained. Carriers are, for example, those mentioned for the solid forms of application. In many cases it is advantageous to use mixtures of different carriers. As dispersing agents there can be used, for example, condensation products of sulfonated naphthalene and sulfonated naphthalene derivatives with formaldehyde, condensation products of naphthalene or naphthalene sulfonic acids with phenol and fomaldehyde, as well as alkali, ammonium and alkaline earth metal salts of lignin sulfonic acid, in addition, alkylaryl sulfonates, alkali and alkaline earth metal salts of dibutyl naphthalene sulfonic acid, fatty alcohol sulfates such as salts of sulfated hexadecanols, heptadecanols, octadecanols, and salts of sulfated fatty alcohol glycol ethers, the sodium salt of oleoyl ethionate, the sodium salt of oleoyl methyl tauride, ditertiary acetylene glycols, dialkyl dilauryl ammonium chloride and fatty acid alkali and alkaline earth metal salts.

Silicones are suitable anti-foam agents.

Active ingredients are mixed, ground, sieved and strained with the additives mentioned above in a way that, in wettable powders, the solid particle size range from 0.02 to 0.04; and in pastes 0.03 mm is not exceeded. To produce emulsifiable concentrates and pastes, dispersing agents such as those given in the previous paragraphs, organic solvents and water are utilized. Examples of suitable solvents are the following: alcohols, benzene, xylenes, toluene, dimethyl sulfoxide, and mineral oil fractions boiling between 120° and 350° C. The solvents must be practically odourless, not phytotoxic, inert to the active substances and not readily inflammable.

Furthermore, the agents according to the invention can be applied in the form of solutions. For this purpose the active ingredients or several active ingredients of general formula I are dissolved in suitable organic solvents, mixtures of solvents or in water. Aliphatic and aromatic hydrocarbons, chlorinated derivatives thereof, alkyl naphthalenes, and mineral oils alone or mixed with each other, can be utilized as organic solvents.

The content of active ingredients in the above described agents is between 0.1 to 95%, in which connection it should be mentioned that in the case of application from aircraft or some other suitable means of application, it is possible to use concentrations of up to 99.5% or even pure active ingredient.

The active ingredients of the formula I can, for example, be formulated as follows:

Dusts

The following substances are used to manufacture (a) a 5% and (b) a 2% dust:
 a. 0.5 parts of active ingredient
    99.5 parts of talcum
 b. 2 parts of active ingredient
    1 part of highly dispersed silica
    97 parts of talcum.

The active ingredients are mixed with the carriers and ground.

Granules a. 5 parts of active ingredients are mixed with
    95 parts of calcium carbonate and the mixture is ground to an average particle size of 80µ.
 b. 5 parts of active ingredient are dissolved in a solvent, e.g. methylene chloride, and the solution is mixed with 2 parts of polyethylene glycol ("Carbowax").
    91.5 parts of calcium carbonate are impregnated with the mixture and
    1.5 parts of precipitated silica are admixed and the solvent is subsequently evaporated.

Bait granules 2.0 parts of active ingredient
0.05 parts of colouring matter
1.0 part of celite or China clay are mixed and finely ground. The granules are then mixed with 96.8 parts of crystallised sugar and impregnated with 0.1 part of an adhesive dissolved, for example, in a small amount of isopropanol, and the solvent is evaporated.

Wettable powder 50 parts of active ingredient
5 parts of a dispersing agent, for example sodium lignin sulphonate,
5 parts of a wetting agent, for example dibutylnaphthalenesulphonic acid
10 parts of silica and
30 parts of China clay are mixed and the mixture is finely ground.

Emulsifiable concentrate 20 parts of active ingredient
20 parts of an emulsifying agent, for example a mixture of alkylarylpolyglycol ether and alkylarylsulphonates, and
60 parts of a solvent, for example xylene, are mixed until the solution is completely homogeneous. This concentrate can be diluted with water to give emulsions of every desired concentration.

Premix (feed additive)

0.25 part of active ingredient
4.75 parts of secondary calcium phosphate, or China clay, aerosil or carbonate of lime, are homogeneously mixed with 95.00 parts of a feed, e.g. rabbit feed.

Aerosol

In an aerosol filling plant
0.25 part of active ingredient and
25.00 parts of 1,1,1-trichloroethane and
24.75 parts of benzene are filled into aerosol containers with
50.00 parts of power gas consisting of freon 11/12 in the ratio 1:1.

Sprays

The following constituents are used to manufacture (a) a 5% and (b) a 2% spray:
a. 5 parts of active ingredient
1 part of epichlorohydrin
94 parts of petroleum ether (boiling limits: 160–190° C).
b. 2 parts of active substance
1 part of diazinone
97 parts of kerosene.

The agents herein described can be mixed with other biocidally active substances or agents. In addition to the cited compounds of the formula I, the new agents may contain, for example, insecticides, fungicides, bactericides, fungistatic agents, bacteriostatic agents, in order to broaden the activity spectrum.

The active compounds of the formula I are applicable as development retardants for combating insects. In contrast to classical insecticides, which, in the form of contact or stomach poisons, kill or paralyse the insects in a few hours, the active compounds of the formula I primarily influence the larval development. They act as larvicides against early instars or by preventing adult emergence from pupae. This activity is not comparable with that of classical insecticides, chemosterilants or juvenile hormones.

Since the active substances of the formula I are not harmful to warm-blooded animals, new horizons are opened up for the principal field of application: that of combating fly maggots. Instead of — as in the case of insecticides — treating large areas, it is possible to administer the active ingredients of the formula I to farm animals, for example hens, with the feed. The active ingredients pass through the alimentary tract unimpaired and are present in the eliminated faeces. The fresh excrement is an ideal breeding ground for hygiene pests, such as flies. The larvae which hatch from the eggs come into immediate contact with the new active compounds and their subsequent development is impaired. The larger maggots which migrate from old to fresh excrement likewise come into contact with the active compounds and their terminal phase is impaired. The maggots pupate without any noteworthy mortality, but no flies emerge from the pupae.

The agents, or the active ingredients contained therein, unfold their growth inhibiting action primarily on the larval and pupal stages of insects, particularly of the order Diptera.

EXAMPLE 1

Test compounds: Active ingredients of the formula I formulated as solutions in acetone.
Test subject: *Musca domestica*
Concentration: 0.05 % of active ingredient
Test method: 5 ml of a 1% solution of active ingredient in acetone are added to 100 grams of CSMA substrate. After thoroughly mixing the treated substrate, the solvent is evaporated. Then 50 one day old *Musca domestica* maggots are added. After 5 days the pupae are separated and after 10 days their hatching rate is determined. The following compounds of formula I show inhibition of adult emergence.

Result

| Compound | n Pupae | n Flies |
|---|---|---|
| 1 | 35 | 0 |
| 2 | 34 | 0 |
| 3 | 39 | 0 |
| 4 | 27 | 0 |
| 6 | 43 | 0 |
| 7 | 50 | 0 |
| 10 | 10 | 0 |
| 11 | 12 | 0 |
| 12 | 45 | 0 |
| 13 | 0 | 0 |
| 14 | 27 | 0 |
| 15 | 4 | 0 |
| Control | 49 | 48 |

EXAMPLE 2

Contact action on *Aedes aegypti* larvae 40 two day old larvae of the yellow-fever mosquito (*Aedes aegypti*) are added to water containing active ingredient (concentration 5 ppm). After the untreated check have emerged to the adult stage, the number of dead, abnormal and normal mosquitoes is determined. The following compounds of formula I demonstrate growth inhibiting effects:

Results

| Compound | Number of pupae | % Mortality |
|---|---|---|
| 1 | 0 | 100 |
| 2 | 0 | 100 |
| 3 | 0 | 100 |
| 6 | 0 | 100 |
| 10 | 0 | 100 |
| 11 | 0 | 100 |
| 13 | 0 | 100 |
| 14 | 6 abnormal pupae giving 3 adults | 75 |
| 15 | 0 | 100 |
| Untreated Control | 40 normal pupae giving 40 normal adults | 0 |

We claim:
1. A method of combating insects which comprises applying to insect larvae, pupae or adults an insecticidally effective amount of a compound of the formula

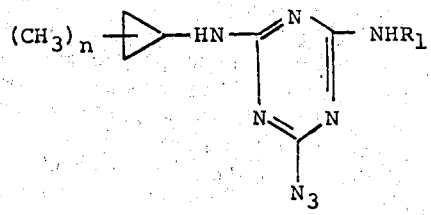

wherein $R_1$ represents hydrogen, cyclopropyl, 1-methylcyclopropyl, 2-methylcyclopropyl, $C_1$–$C_5$ alkyl, $C_3$–$C_4$ alkenyl, $C_3$–$C_4$ alkynyl or $C_1$–$C_5$ alkyl which is substituted by cyano, and $n$ represents 0 or 1.

2. The method according to claim 1, wherein said compound corresponds to the formula

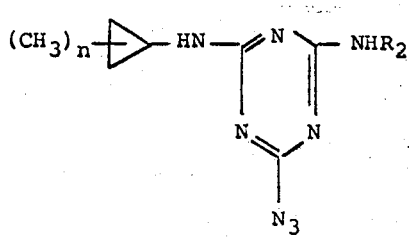

wherein $R_2$ represents cyclopropyl, 2-methylcyclopropyl, methyl, ethyl, n-propyl, isopropyl, n-, i-, sec. and tert. butyl, 1-cyanoethyl or 1-cyanopropyl and $n$ represents 0 or 1.

3. The method according to claim 2, wherein said compound is 4-azido-2-methylamino-6-cyclopropylamino-s-triazine.

4. The method according to claim 2, wherein said compound is 4-azido-2-ethylamino-6-cyclopropylamino-s-triazine.

5. The method according to claim 2, wherein said compound is 4-azido-2,6-bis-cyclopropylamino-s-triazine.

6. The method of claim 1, wherein insects of the order "Diptera" are combatted in the larval stage.

* * * * *